United States Patent [19]

Clitherow

[11] Patent Number: 5,008,256

[45] Date of Patent: Apr. 16, 1991

[54] SALTS OF RANITIDINE AND COMPLEXES OF BISMUTH WITH CARBOXYLIC ACIDS, AND PHARMACEUTICAL COMPOSITIONS THEREOF

[75] Inventor: John W. Clitherow, Sawbridgeworth, England

[73] Assignee: Glaxo Group Limited, England

[21] Appl. No.: 380,378

[22] Filed: Jul. 17, 1989

[30] Foreign Application Priority Data

Jul. 18, 1988 [GB] United Kingdom .................. 8817098
Mar. 1, 1989 [GB] United Kingdom .................. 8904686

[51] Int. Cl.$^5$ ..................... C07F 9/94; C07D 307/52; C07D 307/54
[52] U.S. Cl. ................................... 514/184; 549/206; 549/495
[58] Field of Search ................. 549/206, 495; 514/184

[56] References Cited

U.S. PATENT DOCUMENTS 4,128,658 12/1978 Price et al. .......................... 514/471

FOREIGN PATENT DOCUMENTS 0282131 9/1988 European Pat. Off. .
0282132 9/1988 European Pat. Off. .
1565966 4/1980 United Kingdom .

OTHER PUBLICATIONS

Ward et al., *Proc. Adelaide,* 1979, A30. (abstract).
Bianchi Porro et al., *Scandinavian Journal of Gastroenterology,* 21, Supplement 122, 1986, 39–41.
Lam et al., *Gut,* 1984, 703–706.
Salmon, P. R., *Digestion,* 1987, 37 (suppl. 2), 42–46.
British Pharmaceutical Codex, 1949, "Bismuthi Carbonas", 150–154 and 1183–1185.
S. J. Konturek et al., *Gut,* 1987, 28, pp. 1557–1563.
S. J. Konturek et al., *Scandinavian Journal of Gastroenterology,* 1987, 22, pp. 1059–1063.
R. Iserhard et al., Abstract of a paper given at the 20th Congress of the European Assoc. of Gastroenterology and Endoscopy, Apr. 28–30, 1988.
Lancet (M. Guslandi, 1988, 1(8599), pp. 1383–1385).
M. V. Borkent et al., *Gut,* 1988, 29, pp. 385–389.

*Primary Examiner*—Richard L. Raymond
*Attorney, Agent, or Firm*—Bacon & Thomas

[57] ABSTRACT

The invention relates to salts formed between ranitidine and a complex of bismuth with a carboxylic acid, and solvates of such salts. Examples of suitable carboxylic acids are citric acid, tartaric acid and agaricic acid.

The salts are useful in the treatment of gastrointestinal disorders, particularly gastroduodenal conditions. The salts show the antisecretory activity associated with ranitidine together with antibacterial activity against *Campylobacter pylori* and they also possess cytoprotective properties.

17 Claims, No Drawings

SALTS OF RANITIDINE AND COMPLEXES OF BISMUTH WITH CARBOXYLIC ACIDS, AND PHARMACEUTICAL COMPOSITIONS THEREOF

This invention relates to salts of a furan derivative having action on histamine receptors, to a process for the preparation thereof, to pharmaceutical compositions containing them and to their use in therapeutics. More particularly the invention is concerned with salts of ranitidine formed with bismuth complexes of carboxylic acids.

Ranitidine is the approved name for N-[2-[[[5-[(dimethylamino)-methyl]-2-furanyl]methyl]thio]ethyl]-N'-methyl-2-nitro-1,1-ethenediamine which, together with its physiologically acceptable salts, is described and claimed in British Patent Specification No. 1565966. Reference is made in British Patent Specification No. 1565966 to physiologically acceptable salts formed with inorganic and organic acids. Such salts include hydrochlorides, hydrobromides and sulphates, and salts formed with aliphatic mono- and di-carboxylic acids such as acetates, maleates and fumarates.

Ranitidine is a potent histamine $H_2$-antagonist which, in the form of its hydrochloride salt, is widely used in the treatment of conditions where there is an advantage in lowering gastric acidity. Such conditions include duodenal and gastric ulceration, reflux oesophagitis and Zollinger-Ellison syndrome. Ranitidine may also be used prophylactically in surgical procedures, and in the treatment of allergic and inflammatory conditions where histamine is a known mediator.

Bismuth salts and preparations, such as bismuth citrate, bismuth and ammonium citrate, sodium bismuthyl tartrate, acid bismuth sodium tartrate, acid solution of bismuth, concentrated solution of bismuth, and solution of bismuth and ammonium citrate, which are described in for example the British Pharmaceutical Codex (1949), have long been used as antacids in the treatment of hyperacidity and dyspepsia. In addition, before the advent of histamine $H_2$-antagonists, by which they have now essentially been superceded, such bismuth preparations were also used in the treatment of gastrointestinal ulcers.

In recent years evidence has emerged that *Campylobacter pylori* is associated with histological gastritis, non-ulcer dyspepsia and hypochlorhydria, and may be involved in the pathogenesis of gastric and duodenal ulcer disease.

*Campylobacter pylori* is susceptible to bismuth compounds such as bismuth subcitrate (in the form of, for example, tripotassium dicitrato bismuthate) and bismuth subsalicylate.

A number of the bismuth compounds referred to above are acidic complexes formed between bismuth and a carboxylic acid such as citric or tartaric acid or salts thereof with ammonia or an alkali metal. It has now been found that the basic $H_2$-receptor antagonist ranitidine will form salts with such complexes, and the resulting products possess a useful and advantageous profile of activity.

The present invention thus provides novel salts formed between ranitidine and a complex of bismuth with a carboxylic acid, and solvates of such salts. Suitable carboxylic acids are those which are capable of forming a complex with bismuth, and which complexes are, in turn, capable of forming a salt with ranitidine.

Carboxylic acids which are capable of forming complexes with bismuth to give bismuth-carboxylic acid complexes for use according to the invention may be, for example, carboxylic acids which contain at least three functional groups in addition to the carboxyl group which is available for salt formation with ranitidine. Of the three or more remaining functional groups, three, which may be for example carboxyl and/or hydroxy groups, shall be capable of complexing with trivalent bismuth, to give a trivalent bismuth complex.

In instances where the carboxylic acid can exhibit optical and/or geometric isomerism, the invention is intended to include all optical isomers including racemates, and/or geometric isomers. Solvates, including hydrates, are also included within the scope of the invention.

Examples of suitable carboxylic acids which are capable of forming complexes with bismuth for use according to the invention are citric, tartaric and ethylenediaminetetraacetic acids. Further examples of suitable carboxylic acids are propylcitric and agaricic acids. Tartaric acid and, more especially, citric acid are preferred. Agaricic acid represents a further preferred acid for use according to the invention.

Particular salts according to the invention are N-[2-[[[5-[(dimethylamino)methyl]-2-furanyl]methyl]thio]ethyl]-N'-methyl-2-nitro-1,1-ethenediamine 2-hydroxy-1,2,3-propanetricarboxylate bismuth (3+) complex, also known as ranitidine bismuth citrate; N-methyl-2-[2-[[[5-[(dimethylamino)methyl]-2-furanyl]methyl]thio]ethyl]-N'-nitro-1,1-ethenediamine [(R-R*R*)]-2,3-dihydroxybutanedioate bismuth (3+) complex, also known as ranitidine bismuth tartrate; N-[2-[[[5-[(dimethylamino)methyl]-2-furanyl]methyl]thio]ethyl]-N'-methyl-2-nitro-1,1-ethenediamine 2-hydroxy-1,2,3-nonadecane tricarboxylate bismuth (3+) complex, also known as ranitidine bismuth agaricicate; and N-[2-[[[5-[(dimethylamino)methyl]-2-furanyl]methyl]thio]ethyl]-N'-methyl-2-nitro-1,1-ethenediamine N,N'-ethanediyl-bis[N-(carboxymethyl)-glycine]bismuth (3+) complex, also known as ranitidine bismuth-EDTA.

Preferred salts according to the invention are N-[2-[[[5-[(dimethylamino)methyl]-2-furanyl]methyl]thio]ethyl]-N'-methyl-2-nitro-1,1-ethenediamine 2-hydroxy-1,2,3-propanetricarboxylate bismuth (3+) complex; and N-methyl-2-[2-[[[5-[(dimethylamino)methyl]-2-furanyl]methyl]thio]ethyl]-N'-nitro-1,1-ethenediamine [(R-R*R*)]-2,3-dihydroxybutanedioate bismuth (3+) complex.

Another preferred salt according to the invention is N-[2-[[[5-[(dimethylamino)methyl]-2-furanyl]methyl]thio]ethyl]-N'-methyl-2-nitro-1,1-ethenediamine 2-hydroxy-1,2,3-nonadecane tricarboxylate bismuth (3+) complex.

Ranitidine bismuth citrate represents a particularly preferred compound of the invention.

The salts according to the invention possess a particularly advantageous combination of properties for the treatment of gastrointestinal disorders, especially peptic ulcer disease and other gastroduodenal conditions, for example gastritis and non-ulcer dyspepsia.

Salts according to the invention thus possess the $H_2$-antagonist antisecretory properties associated with ranitidine together with antibacterial activity against *Campylobacter pylori*. In addition, salts of the invention possess cytoprotective properties. They also display activity against the human gastric pepsins, with preferential inhibition of pepsin 1, a pepsin isozyme associated with peptic ulcer.

The antisecretory activity of compounds of compounds according to the invention has been demonstrated in vivo against histamine-induced gastric acid secretion in the Heidenhain pouch dog. The antibacterial activity of the salts against *Campylobacter pylori* and their ability to inhibit human pepsins have been demonstrated in vitro. In addition, antibacterial activity against campylobacter like organisms has been demonstrated in vivo in ferrets. Cytoprotective activity has been demonstrated in vivo by the ability of the salts to inhibit ethanol-induced gastric lesions in rats.

A further feature of the salts according to the invention is that they are water soluble and give stable aqueous solutions. Under normal circumstances many bismuth salts and complexes, including those formed with carboxylic acids of the type used in forming salts of the invention, are insoluble. Bismuth citrate, for example, has a solubility (under neutral aqueous conditions) of only 0.2% on a weight to volume (w/v) basis, whereas ranitidine bismuth citrate is soluble in water to the extent of more than 50% w/v.

Thus the observed properties of salts according to the invention, such as ranitidine bismuth citrate, serve to emphasise the fact that they are distinct chemical entities which can be clearly distinguished from simple mixtures (e.g. admixtures of equimolar proportions) of ranitidine and a complex formed between bismuth and a carboxylic acid.

Salts according to the invention may also be distinguished from simple mixtures of ranitidine and a complex formed between bismuth and a carboxylic acid on the basis of infra-red spectroscopy. Thus there are major spectral changes in going from a simple mixture of ranitidine and a bismuth-carboxylic acid complex to a salt according to the invention. The infra-red spectrum of a simple physical mixture of ranitidine and bismuth citrate, for example, has major peaks at $v_{max}$ 1131, 988 and 603 cm$^{-1}$ which are absent in the infra-red spectrum of ranitidine bismuth citrate.

Salts according to the invention may be prepared by reacting ranitidine with an appropriate bismuth - carboxylic acid complex (e.g. bismuth citrate or bismuth ammonium citrate), in a suitable solvent such as water, and separating the salt thus formed from the solution.

According to a further aspect the invention provides a salt formed between ranitidine and a complex of bismuth with a carboxylic acid, including solvates of such salts, said salt being prepared by reacting ranitidine with a bismuth carboxylic acid complex.

According to one particular further aspect, the invention provides ranitidine bismuth citrate, including solvates thereof when prepared by reacting ranitidine with a complex of bismuth with citric acid.

The reaction between ranitidine and an appropriate bismuth-carboxylic acid complex to give a salt according to the invention is preferably carried out at elevated temperature for example at a temperature within the range of 40° to 100° C. Once the reaction is complete (when for example the mixture has reached neutrality as judged by pH and/or dissolution is complete), the suspension or solution is cooled and filtered, and the required ranitidine salt may be obtained from the filtrate, by evaporation followed by extraction and trituration of the resulting residue using for example an alcohol e.g. methanol or ethanol, a ketone e.g. acetone or an ether e.g. diethyl ether. Alternatively, the reaction mixture may be evaporated directly, followed by extraction and trituration of the resulting residue. Further alternative procedures for isolating the desired salt include spray drying of the filtrate, or addition of the filtrate (optionally after dilution with e.g. water) to a suitable anti-solvent (e.g. an alcohol such as ethanol) at an elevated temperature (e.g. the reflux temperature of the anti-solvent) which results in precipitation of the product.

The intermediate bismuth - carboxylic acid complexes may in general be prepared by the procedures described in the British Pharmaceutical Codex (1949). Thus, for example, a suspension of a suitable bismuth salt (e.g. bismuth oxynitrate) and an appropriate carboxylic acid (e.g. citric or tartaric acid) in a solvent such as water may be heated at for example 90° to 100° C., the reaction being judged as complete when for example one drop of the mixture yields a clear solution when added to weak aqueous ammonia. The suspension is then optionally diluted with water, and the desired bismuth-carboxylic acid complex may be recovered by filtration. Bismuth ammonium citrate may for example be prepared, in situ if desired, by treating bismuth citrate with an appropriate amount of aqueous ammonia.

The salts according to the invention may be formulated for administration in any convenient way and the invention includes within its scope pharmaceutical compositions containing a salt according to the invention adapted for use in human or veterinary medicine. Such compositions, which are primarily intended for oral administration, may be formulated in a conventional manner using one or more pharmaceutically acceptable carriers or excipients. Tablets represent a preferred type of composition.

For oral administration, the pharmaceutical compositions may take the form of, for example, tablets (including chewable or suckable tablets) or capsules. Such compositions may be prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

A proposed dose of the salts of the invention for internal administration to man is 100 mg to 1 g, preferably 100 to 800 mg, more particularly 150 to 600 mg, of the active ingredient per unit dose. The unit dose may be administered, for example, one to four times daily, preferably once or twice. The exact dose will depend on the nature and severity of the condition being treated, and it will also be appreciated that it may be necessary to make routine variations to the dosage depending on the age and weight of the patient.

The invention is illustrated by the following Examples in which temperatures are in °C. Thin layer chromatography (t.l.c.) was carried out on silica, eluting with dichloromethane:ethanol:0.88 ammonia, 70:8:1 (System A) or ethyl acetate:isopropanol:0.88 ammonia:water, 25:15:4:2 (System B), and using u.v., iodoplatinate and potassium permanganate for detection, unless indicated otherwise.

PREPARATION 1

2-Hydroxy-1,2,3-propanetricarboxylic acid, bismuth (3+) complex (1:1)

("Bismuth citrate")

A mixture of bismuth oxynitrate (22.96 g) and citric acid (33.60 g) in water (80 ml) was heated on a steam bath with frequent stirring for 30 min, by which time one drop of the suspension added to weak aqueous ammonia gave a clear solution. The mixture was diluted with water, filtered, and the residue washed well with water until free of nitrate and excess citric acid. The residue was dried under vacuum to give the title compound (32.18 g).

Analysis Found: C,18.08; H,1.34; O,28.80; Bi,52. $C_6H_5BiO_7.0.11H_2O$ requires C,18.01; H,1.32; O,28.44; Bi,52.2%.

Water assay indicated 0.49% $H_2O \equiv 0.11$ mol.

PREPARATION 2

[R-(R*R*)]-2,3-Dihydroxybutanedioic acid, bismuth (3+) complex (2:1)

("Bismuth tartrate")

A mixture of (+)-tartaric acid (27 g) and bismuth oxynitrate (8.61 g) in water (50 ml) was heated at 90°-100° with occassional stirring for 30 min, by which time a small portion of the product dissolved completely in weak aqueous ammonia. The mixture was cooled to room temperature then filtered and the filtrate washed well with water until free from water soluble materials. The residue was dried at 70°-80° in vacuo to give the title compound (14.78 g).

Analysis Found: C,18.44; H,1.81; O,39.04; Bi,40. $C_8H_9Bi.O_{12}.0.43H_2O$ requires C,18.70; H,1.93; O,38.70; Bi,40.7%.

Water assay indicated 1.54% $H_2O \equiv 0.43$ mol.

PREPARATION 3

2-Hydroxy-1,2,3-nonadecanetricarboxylic acid, bismuth (3+) complex (1:1) ("Bismuth agaricicate")

A mixture of (−)-2-hydroxy-1,2,3-nonadecanetricarboxylic acid (agaricic acid, 9.15 g) and bismuth oxynitrate (5.74 g) in water (50 ml) was heated at 90°-95° for 4 h. The acidic mixture was filtered and the residue washed well with water until the filtrates were neutral. The residue was washed well with hot methanol (3×50 ml) then dried to give the title compound (12.286 g).

Analysis Found: C,43.52; H,6.34; O,18.49; Bi,31. $C_{22}H_{37}BiO_7.0.1C_{22}H_{40}O_7.0.11H_2O$ requires C,43.63; H,6.24; O,18.76%; Bi,31.4%.

Water assay indicated 0.31% $H_2O \equiv 0.11$ mol.

PREPARATION 4

N,N'-1,2-Ethanediylbis[N-(carboxymethyl)glycine]bismuth (3+) complex (1:1) ("Bismuth-EDTA")

A mixture of bismuth oxynitrate (20.09 g) and N,N'-1,2-ethanediylbis[N-(carboxymethyl)glycine] (EDTA; 17.57 g) in water (100 ml) was heated at 90°-95° for 2 h. The hot suspension was filtered and the residue reheated at 90°-95° with water (4×70 ml) until almost all the solid had dissolved. On each extraction, the suspension was filtered and the strongly acidic filtrates evaporated in vacuo to approximately 70 ml. The mixture from the extractions was cooled to 18° and the precipitated solid filtered off and washed free of nitric acid with cold water, then ethanol and ether, and dried to give the title compound (18.52 g).

Analysis Found: C,23.27; H,2.49; N,5.41; O,26.43; Bi,41. $C_{19}H_{13}BiN_2O_8.0.5H_2O$ requires C,23.68; H,2.78; N,5.52; O,26.81; Bi,41.2%.

Water assay indicated 1.819% $H_2O \equiv 0.5$ mol.

EXAMPLE 1

N-[2-[[[5-[(Dimethylamino)methyl]-2-furanyl]methyl]thio]ethyl]-N'-methyl-2-nitro-1,1-ethenediamine 2-hydroxy-1,2,3-propanetricarboxylate bismuth (3+) complex (1:1:1) ("Ranitidine bismuth citrate")

A mixture of bismuth citrate (2.08 g) and N-[2-[[[5-[(dimethylamino)methyl]-2-furanyl]methyl]thio]ethyl]-N'-methyl-2-nitro-1,1-ethene diamine (ranitidine; 1.57 g) in water (15 ml) was heated at 90°-95° until the suspension became neutral to pH paper (ca 15 min). The mixture was cooled to room temperature and unreacted bismuth citrate (0.657 g) was filtered off. The filtrate was evaporated to dryness in vacuo to give a hard gum. Methanol (50 ml) was added to the gum, and the mixture evaporated to give a residue which was heated with methanol (70 ml) and cooled. The cloudy supernatant liquid was decanted off and the residue triturated to a powder with methanol (50 ml) and the suspension filtered. The residue was washed with methanol and dried to give the title compound (1.98 g). T.l.c. (System A) Rf 0.35 (ranitidine) and Rf zero (bismuth citrate).

Analysis Found: C,30.67; H,3.97; N,7.10; O,23.60; S,3.97; Bi,29. $C_{19}H_{27}BiN_4O_{10}S.0.1C_6H_5BiO_7.0.16C_2H_5OH.0.48H_2O$ requires C,31.14; H,3.86; N,7.29; O,23.65; S,4.17; Bi,29.9%.

Water assay indicated 1.06% $H_2O \equiv 0.48$ mol. N.m.r. indicated 0.16 mol ethanol.

EXAMPLE 2

N-[2-[[[5-[(Dimethylamino)methyl]-2-furanyl]methyl]thio]ethyl]-N'-methyl-2-nitro-1,1-ethenediamine 2-hydroxy-1,2,3-propanetricarboxylate bismuth (3+) complex (1:1:1) ("Ranitidine bismuth citrate")

To a mixture of bismuth citrate (3.98 g.) with water (15 ml) was added sufficient aqueous 0.88 ammonia to dissolve the solid. The solution was filtered through Hyflo and the combined filtrate and washings evaporated in vacuo. The solution was re-evaporated with water until the supernatant vapour above the residue was no longer basic to pH 1-14 paper (water 5×70 ml). To a solution of the residue in water (30 ml) was added ranitidine (3.14 g) and the solution which formed was evaporated to dryness in vacuo. The water soluble residue was re-evaporated with water until no more basic vapour was detectable (16×80 ml). The residue was dried by rotary evaporation under vacuum at 80°-90° and the powdery residue removed with the aid of ether. The residue was ground to a fine powder which was suspended in ether and filtered. The resulting product was dried to give the title compound (6.814 g). T.l.c. (System A) Rf 0.3 (ranitidine) and Rf zero (bismuth citrate).

N.m.r. δ(DMSO-d$_6$) 2.57 (2H,d,½ AB of CH$_2$CO), 2.8-2.9 (m, CH$_3$NH, CH$_2$CH$_2$S and ½ AB of CH$_2$CO), 2.87 (s, CH$_3$)$_2$N+), 3.47 (2H,t, CH$_2$CH$_2$NH), 3.86 (2H,s,CH$_2$S), 4.35 (2H,s,CH$_2$N+), 6.10 and 6.67 (2H, d+d, furan =CH's).

I.r. ν$_{max}$ (Nujol) 3454 (—OH), 3267 and 3200 (—NH—), and 1620, 1570 and 1260 (—NHC(=C-HNO$_2$)NH—+—CO$_2$−)cm$^{-1}$.

Analysis Found: C,31.54; H,4.04; N,8.02; O,23.31; S,4.32; Bi,28.

C$_{13}$H$_{22}$N$_4$O$_3$S.C$_6$H$_5$BiO$_7$.0.34H$_2$O requires C,31.75; H,3.88; N,7.80; O,23.02; S,4.46%; Bi,29.1%.

Water assay indicated 0.85% H$_2$O≡0.34 mol.

EXAMPLE 3

N-[2-[[[5-[(Dimethylamino)methyl]-2-furanyl]methyl]-thio]ethyl]-N'-methyl-2-nitro-1,1-ethenediamine 2-hydroxy-1,2,3-propanetricarboxylate bismuth (3+) complex (1:1:1) ("Ranitidine bismuth citrate")

A mixture of ranitidine (44.0 g) and bismuth citrate (40.0 g) in water (70 ml) was heated at 90°-95° for 30 minutes. The cloudy solution was filtered, diluted with water (20 ml) then added over 23 minutes with stirring to industrial methylated spirit (IMS; 2.4 liters), heated under reflux. The resulting suspension was heated for 15 minutes then cooled to ambient temperature. The title compound (63.0 g) was collected by filtration, washed with IMS (2×200 ml) and dried in vacuo at 40°. T.l.c. (System B) Rf 0.49 (ranitidine) and Rf zero (bismuth citrate), detection: u.v., iodine.

EXAMPLE 4

N-[2-[[[5-[(Dimethylamino)methyl]-2-furanyl]methyl]-thio]ethyl]-N'-methyl-2-nitro-1,1-ethenediamine 2-hydroxy-1,2,3-propanetricarboxylate bismuth (3+) complex (1:1:1) ("Ranitidine bismuth citrate")

Ranitidine (44.0 g) was added to a suspension of bismuth citrate (55.7 g) in 1.0 molar aqueous ammonia (56 ml) and water (92 ml). The suspension was heated at 90° for 5 minutes then the resulting cloudy solution was filtered and diluted with water (10 ml). The title compound (10.3 g) was isolated by spray drying the resulting solution (40 ml of a total volume of 195 ml). T.l.c. (System B) Rf 0.49 (ranitidine) and Rf zero (bismuth citrate), detection: u.v., iodine.

EXAMPLE 5

N-[2-[[[5-[(Dimethylamino)methyl]-2-furanyl]methyl]-thio]ethyl]-N'-methyl-2-nitro-1,1-ethenediamine [(R-(R*R*)]-2,3-dihydroxybutanedioate bismuth (3+) complex (1:1:1) ("Ranitidine bismuth tartrate")

Ranitidine (5.02 g) was added to a slurry of bismuth tartrate (2.02 g) in water (10 ml) and the mixture warmed gently with stirring until solution was effected. The solution was filtered through Hyflo and the combined filtrate and washings evaporated in vacuo to give a thick gum which became a frothy solid on further evaporation. This was re-evaporated with methanol (3×50 ml) and the gummy residue extracted with hot methanol (50 ml×3). The semi-solid residue was triturated with methanol (20 ml) until a cream coloured fine suspension was formed which was filtered. The residue was reduced to a fine suspension by trituration of the residue with methanol (20 ml) then filtered and the residue washed with methanol then ether and dried to give the title compound (1.853 g). T.l.c. (System A) Rf 0.35 (ranitidine) and Rf zero (bismuth tartrate).

I.r. ν$_{max}$ (KBr) 3600-2000 (complex series of bands, —NH—+—OH), 1750-1500 (series of bands, —NHC(=CHNO$_2$)NH—+—CO$_2$−+—CO$_2$H), and 1233 (—NHC(=CHNO$_2$)NH—)cm$^{-1}$.

Analysis Found: C,28.03; H,3.59; N,6.84; O,24.85; S,3.87. C$_{13}$H$_{22}$N$_4$O$_3$S.C$_4$H$_3$O$_6$Bi.0.33C$_8$H$_9$BiO$_{12}$.0.15CH$_3$OH requires C,28.22; H,3.42; N,6.65; O,24.90; S,3.81%.

N.m.r. indicated 0.15 mol methanol.

EXAMPLE 6

N-[2-[[[5-[(Dimethylamino)methyl]-2-furanyl]methyl]-thio]ethyl]-N'-methyl-2-nitro-1,1-ethenediamine 2-hydroxy-1,2,3-nonadecane tricarboxylate bismuth (3+) complex (1:1:1) ("Ranitidine bismuth agaricicate")

A mixture of bismuth agaricicate (containing agaricic acid, 0.1 mol and water, 0.11 mol) (4.26 g) and ranitidine (3.77 g) in water (10 ml) was heated at 90°-95° for 4 h. The solution was diluted with water (15 ml) and the heating continued for 1 h. The opalescent liquid was filtered through Hyflo whilst hot and the filtrate evaporated to dryness with the aid of ethanol. The gummy residue was re-evaporated with ethanol (3×30 ml) to give a gum. This was dissolved in ethanol (50 ml) and the solution filtered through Hyflo. The combined filtrate and washings were evaporated in vacuo to give a gum. This was mixed with hot acetone (70 ml) and, after heating the mixture for 10 min, the supernatant liquid was decanted off. This procedure was repeated and the semi-solid residue triturated with acetone (50 ml) to give a fine suspension. This was filtered off and the residue washed well with acetone and dried to give the title compound (4.69 g) as a buff coloured solid.

Analysis Found: C,45.37; H,6.50; N,5.36; O,17.43; S,3.01. C$_{35}$H$_{59}$N$_4$O$_{10}$SBi.0.05C$_{22}$H$_{40}$O$_7$.0.5H$_2$O requires C,44.85; H,6.46; N,5.80; O,17.96; S,3.32%.

Water assay indicated 1.04% H$_2$O≡0.5 mol.

T.l.c. (System A) Rf 0.35 (ranitidine) and Rf zero (bismuth agaricicate/agaricic acid). T.l.c. (Chloroform:methanol:acetic acid:water, 15:5:1:1) Rf 0.3 (ranitidine), detection: u.v, iodoplatinate, potassium permanganate and bromocresol green stain and Rf 0.6 (agaricic acid), detection: bromocresol green stain.

EXAMPLE 7

N-[2-[[[5-[(Dimethylamino)methyl]-2-furanyl]methyl]-thio]ethyl]-N'-methyl-2-nitro-1,1-ethenediamine N,N'-ethanediylbis[N-(carboxymethyl)-glycine]bismuth (3+) complex (1:1:1) ("Ranitidine bismuth-EDTA")

To a mixture of bismuth-EDTA (2.99 g) and ranitidine (2.2 g) was added water (15 ml) and the mixture warmed to effect complete solution. A small amount of precipitate which formed was filtered off through Hyflo. The solution was evaporated to dryness in vacuo and the residue re-evaporated with methanol (2×15 ml). The residue was dissolved in warm methanol (20 ml) and the solution filtered through Hyflo. The filtrate was evaporated to dryness to give a semi solid which was dissolved in methanol (10 ml). Cooling caused precipitation of an oil and after standing for 60 h, a white solid formed. This was filtered off and the residue washed with methanol. The solid was re-suspended in ethanol and filtered and the residue washed with methanol. The solid was re-suspended in ethanol and filtered and the residue washed with ethanol then ether and dried to give the title compound (3.786 g). T.l.c. (System A) Rf 0.35 (ranitidine) and Rf zero (Bismuth-EDTA).

Analysis Found: C,33.57; H,4.45; N,10.09; S,3.70; Bi,24. $C_{13}H_{22}N_4O_3S.C_{10}H_{13}BiN_2O_8.H_2O$ requires C,33.26; H,4.49; N,10.12; S,3.86; Bi,25.2%.

Water assay indicated 2.24% $H_2O \equiv 1.0$ mole.

The following Examples A to D illustrate pharmaceutical compositions according to the invention in which the active ingredient is in particular ranitidine bismuth citrate. Other compounds according to the invention may be formulated in a similar manner.

EXAMPLE A

Tablets

Tablets may be prepared by the normal methods such as direct compression or wet granulation.

The tablets may be film coated with suitable film forming materials, such as hydroxypropyl methylcellulose, using standard techniques.

| (i) Direct Compression | mg/tablet |
| --- | --- |
| Active ingredient | 380 mg |
| Lactose | 145 mg |
| Microcrystalline Cellulose | 140 mg |
| Cross-linked Polyvinylpyrrolidone | 28 mg |
| Magnesium Stearate | 7 mg |
| Compression weight | 700 mg |

The active ingredient, microcrystalline cellulose, lactose and cross-linked polyvinylpyrrolidone are sieved through a 500 μm sieve and blended in a suitable mixer. The magnesium stearate is sieved through a 250 μm sieve and blended with the active blend. The blend is compressed into tablets using suitable punches.

| (ii) Wet Granulation | mg/tablet |
| --- | --- |
| Active ingredient | 380 mg |
| Lactose | 215 mg |
| Pregelatinised Starch | 70 mg |
| Cross-linked Polyvinylpyrrolidone | 28 mg |
| Magnesium Stearate | 7 mg |
| Compression weight | 700 mg |

The active ingredient, lactose and pregelatinised starch are blended together and granulated with water. The wet mass is dried and milled. The magnesium stearate and cross-linked polyvinylpyrrolidone are screened through a 250 μm sieve and blended with the granule. The resultant blend is compressed using suitable tablet punches.

EXAMPLE B

Suckable/Chewable Tablets

| | | mg/tablet |
| --- | --- | --- |
| (i) Active ingredient | | 380 mg |
| Polyvinylpyrrolidone | | 28 mg |
| Sweetener/Flavour | | qs |
| Magnesium Stearate | | 7 mg |
| Mannitol | to | 700 mg |
| Compression weight | | 700 mg |

The active ingredient, sweetener/flavour and mannitol are blended together and granulated with a solution of polyvinylpyrrolidone. The wet mass is dried, milled and lubricated with magnesium stearate (meshed through a 250 μm sieve). The resultant granule is compressed into tablets using suitable punches.

| | | mg/tablet |
| --- | --- | --- |
| (ii) Active ingredient | | 380 mg |
| Hydroxypropyl methylcellulose | | 20 mg |
| Magnesium Stearate | | 7 mg |
| Flavour | | qs |
| Xylitol | to | 700 mg |
| Compression weight | | 700 mg |

The active ingredient, xylitol and flavour are blended together, granulated using a solution of the hydroxypropyl methylcellulose in aqueous ethanol, and dried. The granule is milled, lubricated with magnesium stearate (meshed through a 250 μm sieve) and compressed into tablets using suitable punches.

EXAMPLE C

Capsules

| | | mg/capsule |
| --- | --- | --- |
| (i) | Active ingredient | 380 mg |
| | Pregelatinised Starch | 65 mg |
| | Magnesium Stearate | 5 mg |
| | Fill weight | 450 mg |

The active ingredient and pregelatinised starch are screened through a 500 μg mesh sieve, blended together and lubricated with magnesium stearate (meshed through a 250 μm sieve). The blend is filled into hard gelatin capsules of a suitable size.

| | | mg/capsule |
| --- | --- | --- |
| (ii) | Active ingredient | 380 mg |
| | Lactose | 75 mg |

-continued

|  | mg/capsule |
|---|---|
| Polyvinylpyrrolidone | 20 mg |
| Cross-linked Polyvinylpyrrolidone | 20 mg |
| Magnesium Stearate | 5 mg |
| Fill weight | 500 mg |

The active ingredient and lactose are blended together and wet massed with a solution of polyvinylpyrrolidone. The mass is dried and milled and blended with cross-linked polyvinylpyrrolidone and magnesium stearate (screened through a 250 μm mesh). The resultant blend is filled into hard gelatin capsules of a suitable size.

EXAMPLE D

Oral Syrup

| Active ingredient | | 380 mg |
|---|---|---|
| Hydroxypropyl Methylcellulose | | 45 mg |
| Propyl Hydroxybenzoate | | 1.5 mg |
| Butyl Hydroxybenzoate | | 0.75 mg |
| Saccharin Sodium | | 5 mg |
| Sorbitol Solution | | 1.0 ml |
| Suitable Buffers | | qs |
| Suitable Flavours | | qs |
| Purified Water | to | 10 ml |

The hydroxpropyl methylcellulose is dispersed in a portion of hot purified water together with the hydroxybenzoates and the solution is allowed to cool to room temperature. The saccharin sodium, flavours and sorbitol solution are added to the bulk solution. The active ingredient is dissolved in a portion of the remaining water and added to the bulk solution. Suitable buffers may be added to control the pH in the region of maxiumum stability. The solution is made up to volume, filtered and filled into suitable containers.

I claim:

1. A salt formed between ranitidine and a complex of bismuth with a carboxylic acid, or a solvate of such a salt.

2. A salt according to claim 1, wherein said carboxylic acid contains at least three functional groups in the molecule in addition to the carboxyl group which is available for salt formation with ranitidine.

3. A salt according to claim 1, wherein said carboxylic acid is selected from the group consisting of citric acid, tartaric acid, ethylenediaminetetraacetic acid, propylcitric acid and agaricic acid.

4. A salt according to claim 1, wherein said carboxylic acid is selected from the group consisting of citric acid and tartaric acid.

5. A compound selected from the group consisting of N-[2-[[[5-[(dimethylamino)methyl]-2-furanyl]methyl]thio]ethyl]-N'-methyl-2-nitro-1,1-ethenediamine 2-hydroxy-1,2,3-propanetricarboxylate bismuth (3+) complex and its solvates.

6. A compound selected from the group consisting of N-[2-[[[5-[(dimethylamino)methyl]-2-furanyl]methyl]thio]ethyl]-N'-methyl-2-nitro-1,1-ethenediamine [(R-R*R*)]-2,3-dihydroxybutanedioate bismuth (3+) complex and its solvates.

7. A pharmaceutical composition for the treatment of a gastrointestinal disorder comprising an effective amount for treatment of said disorder of a salt formed between ranitidine and a complex of bismuth with a carboxylic acid, or a solvate of such a salt, together with at least one pharmaceutically acceptable carrier or diluent.

8. A pharmaceutical composition according to claim 7, wherein said carboxylic acid is selected from the group consisting of citric acid and tartaric acid.

9. A pharmaceutical composition according to claim 7, in a form adapted for oral administration.

10. A pharmaceutical composition for the treatment of a gastrointestinal disorder comprising an effective amount for treatment of said disorder of N-[2-[[[5-[(dimethylamino)methyl]-2-furanyl]methyl]thio]ethyl]-N'-methyl-2-nitro-1,1-ethenediamine 2-hydroxy-1,2,3-propanetricarboxylate bismuth (3+) complex, or a solvate thereof, together with at least one pharmaceutically acceptable carrier or diluent.

11. A pharmaceutical composition according to claim 10, in unit dose form containing 100 mg to 1 g of said complex per unit dose.

12. A pharmaceutical composition according to claim 10 in unit dose form containing 100 to 800 mg of said complex per unit dose.

13. A pharmaceutical composition according to claim 10, in unit dose form containing 150 to 600 mg of said complex per unit dose.

14. A pharmaceutical composition according to claim 10 in a form adapted for oral administration.

15. A pharmaceutical composition according to claim 14 in the form of tablets.

16. A salt formed between ranitidine and a complex of bismuth with a carboxylic acid, or a solvate of such a salt, the said salt having been prepared by reacting ranitidine with a bismuth carboxylic acid complex.

17. Ranitidine bismuth citrate or a solvate thereof, when prepared by reacting ranitidine with a complex of bismuth with citric acid.

* * * * *

UNITED STATES PATENT AND TRADEMARK OFFICE

CERTIFICATE EXTENDING PATENT TERM
UNDER 35 U.S.C. § 156

PATENT NO.      :   5,008,256

ISSUED          :   April 16, 1991

INVENTOR(S)     :   John W. Clitherow

PATENT OWNER    :   Glaxo Group Limited

PRODUCT         :   TRITEC® (ranitidine bismuth citrate)

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 387 days from July 17, 2009, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 23rd day of October 1998.

Bruce A. Lehman
Assistant Secretary of Commerce and
   Commissioner of Patents and Trademarks